United States Patent [19]

LeVeen et al.

[11] 4,390,019

[45] Jun. 28, 1983

[54] BLOOD VESSEL CLAMP

[76] Inventors: Harry H. LeVeen, 800 Poly Pl., Brooklyn, N.Y. 11209; Eric G. LeVeen, 333 East 49th St., New York, N.Y. 10017

[21] Appl. No.: 15,969

[22] Filed: Feb. 28, 1979

[51] Int. Cl.³ ............................................. A61B 17/12
[52] U.S. Cl. .................................... 128/325; 128/346
[58] Field of Search ...................... 128/346, 325, 322; 251/9, 10; 24/236, 237, 248 B, 255 SL, 255 R

[56] References Cited

U.S. PATENT DOCUMENTS

| D. 234,204 | 1/1975 | Miller et al. | 24/255 SL X |
|---|---|---|---|
| 2,215,725 | 9/1940 | Martinson | 128/346 X |
| 3,247,852 | 4/1966 | Schneider | 128/346 |
| 3,503,398 | 3/1970 | Fogarty et al. | 128/322 X |
| 4,112,944 | 9/1978 | Williams | 128/346 X |

*Primary Examiner*—Michael H. Thaler
*Attorney, Agent, or Firm*—Brooks, Haidt, Haffner & Delahunty

[57] ABSTRACT

A surgical clamp having a one-piece body of resilient plastics material with a soft, resilient strip at the clamping surfaces. The clamp body has two arms joined by a resilient member which normally spreads the arms apart but which permits the arms to be pressed into generally parallel clamping positions. The arms are held in various relative positions by a ratchet which extends from one arm and engages the other arm and which permits adjustment of clamping pressure. The arms also have projections adjacent to the clamping surfaces thereof which prevent sideways dislodgement of a clamped part.

6 Claims, 5 Drawing Figures

BLOOD VESSEL CLAMP

This invention relates to a surgical clamp and particularly, to a clamp for stopping the flow of blood from a blood vessel.

In the course of vascular surgery, it is often necessary to occlude temporarily a major artery in order to repair it, to clean out its contents or to anastomose it to another blood vessel. Usually an occluding clamp is used, and the clamp must not only gently squeeze the vessel but also must evenly compress the vessel without injury. A spring loaded clamp with fixed tension is not satisfactory, and provision must be made for adjustment of the clamping pressure. Thus, the pressure must not be more than necessary to occlude the blood vessel, and gradual release of the pressure is desirable to initially permit a small flow of blood to test any suturing before the clamp is fully opened. Also, after the clamp is applied, it should not have an opening through which the vessel can be accidently dislodged and cause a serious loss of blood.

Various types of clamps with soft, vessel engaging surfaces and ratchet type holding mechanisms are known in the art. See, for example, U.S. Pat. Nos. 3,174,754; 3,503,398; and 3,766,925. Some of the prior art clamps are cumbersome or awkward to use and/or expensive to make. After extensive experimentation, we have discovered a clamp construction which has the features described hereinbefore and which is both simple and inexpensive to make.

One object of the invention is a simple surgical clamp which is readily applied to a blood vessel, which is easily adjustable, which will provide the desired clamping pressure without injury to a vessel and which, after application, does not have a side opening through which the vessel can be displaced.

In the preferred embodiment of the clamp of the invention at least the major portion of the clamp is made in one piece from a plastics material. The major portion comprises a pair of clamping arms which are generally parallel when the clamp is closed. The arms are interconnected at one end by a flexible, resilient member which urges the arms into separated relation. The opposite end of one arm carries a ratchet which extends toward and engages the opposite end of the other arm so as to hold the arms in positions at which they are set as the clamp is applied. However, the other arm can be released from the ratchet to decrease clamping pressure or to open the clamp for insertion of a blood vessel between the clamping arms.

The clamping portions of the arms have slots for receiving extensions of a soft, resilient strip for engaging the blood vessel. The clamping portion of one arm has a projection or tail at one end for preventing dislodgement of a blood vessel in one direction, and the clamping portion of the other arm has a similar projection or tail displaced from the first-mentioned projection for preventing dislodgement of a blood vessel in the opposite direction.

Other objects and advantages of the present invention will be apparent from the following detailed description of the presently preferred embodiment thereof, which description should be considered in conjunction with the accompanying drawings in which.

Figure 1:
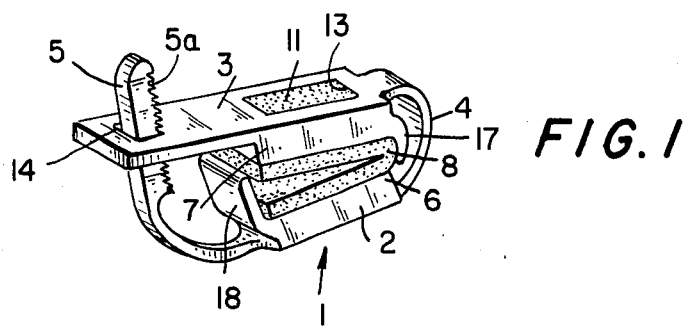
FIG. 1 is an isometric view of the preferred embodiment of the clamp of the invention.
Figure 2:
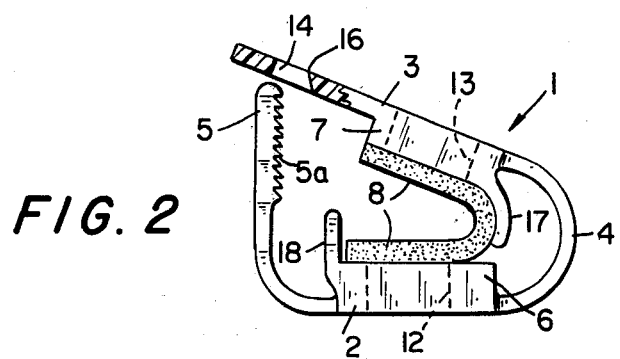
FIG. 2 is a side elevation view of the embodiment shown in FIG. 1 with the clamp in its released position.

In the preferred embodiment of the invention illustrated in the drawings, the clamp 1 has a pair of clamping arms 2 and 3 which are integral with a resilient member 4 which, when the ratchet 5, hereinafter described, is released, causes the arms 2 and 3 to move apart and assume the positions shown in FIG. 2. The member 4 also has sufficient elasticity to permit the arms 2 and 3 to be spread further apart than is shown in FIG. 2 so that a blood vessel can be inserted between the arm 3 and the upper end of the ratchet 5 during application of the clamp 1 to a blood vessel. Of course, it is not necessary that the blood vessel be so inserted because the end of the vessel can be inserted directly into the space between the arms 2 and 3 shown in FIG. 2.

Figure 3:
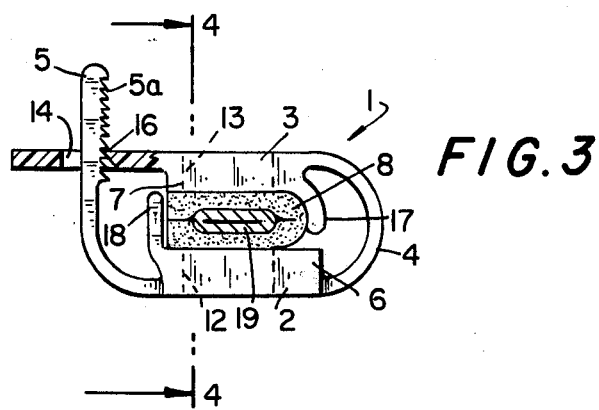
FIG. 3 is a side elevation view of the embodiment shown in FIG. 1 with the clamp receiving and clamping a blood vessel.

The member 4 also has sufficient resiliency to permit the arms 2 and 3 to be brought into parallel, or substantially parallel relation, as shown in FIG. 3.

Figure 4:
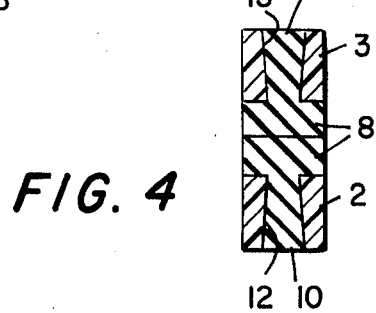
FIG. 4 is a cross-sectional view of the embodiment shown in FIG. 3 and is taken along the line 4—4 indicated in FIG. 3.
Figure 5:
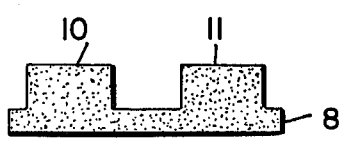
FIG. 5 is a side elevation view of the soft resilient strip forming part of the clamp of the invention.

The clamping arms 2 and 3 respectively have an intermediate part engaging, clamping portion 6 and 7, the clamping portion 6 extending toward the arm 3 and the clamping portion 7 extending toward the arm 2. A strip 8 of soft, resilient material, i.e. softer than the material of the portions 6 and 7, is on the facing surfaces of the portions 6 and 7. The strip 8, preferably is a single strip, as illustrated in FIG. 5, and has a pair of projections 10 and 11 which are received in slots 12 and 13 in the portions 6 and 7 and the arms 2 and 3. The slots 12 and 13 are tapered, as shown in FIG. 4, and the dimensions of the projections 10 and 11 are such as to fill the slots 12 and 13 as to resist dislodgement of the projections 10 and 13 from the slots 12 and 13. However, the strip 8 may be removed and replaced. Although the strip 18 is a single strip for manufacturing and blood vessel retention reasons, the strip 8 could be two separate and identical pieces.

The ratchet 5, having ratchet teeth 5a, extends from the end of the arm 2 opposite from the end thereof which is connected to the member 4 and extends toward the arm 3 which has an opening 14 therein through which the ratchet 5 can pass. The ratchet 5 is made of resilient material and is formed so that it is urged toward a lip 16 at one side of the opening 14. Thus, after the ratchet 5 is inserted into the opening 14, with pressing of the arms 2 and 3 toward each other, the ratchet teeth 5a will engage the lip 16 when the arms 2 and 3 are released and will prevent separation of the arms 2 and 3 until the ratchet 5 is moved in a direction away from the lip 16. It will be observed that the width of the opening 14 between the lip 16 and the opposite side of the opening is greater than the corresponding dimension of the ratchet 5.

A projection, or tail, 17 extends from the end of the clamping portion 7 nearest the member 4 and a corresponding projection, or tail, 18 extends from the end of the clamping portion 6 farthest from the member 4. Such projections 17 and 18 prevent a blood vessel from being dislodged from between the clamping portions 6 and 7 when the clamp is applied. Of course, if desired, the projection 17 could extend from the opposite end of the clamping portion 7 if the projection 18 extends from the opposite end of the clamping portion 6.

Preferably, all the parts of the clamp 1, except the strip 8, are injection molded in one piece from a plastics material, such as a polycarbonate, and the strip 8 is made from soft, resilient material such as a soft or sponge rubber or a cellular plastics material, such as polyurethane.

In use, a blood vessel, e.g. the blood vessel 19 (FIG. 3) is inserted between the facing surfaces of the strip 8 with the clamp 1 open, as shown in FIG. 2, or with the facing surfaces of the strip 8 otherwise far enough apart to receive the blood vessel 19. The arms 2 and 3 are then pressed toward each other, with the ratchet 5 received in the opening 14, until the flow of blood from the vessel 19 is stopped and until the desired pressure, a matter of "feel" and visual observation, is applied to the vessel 19. The pressure may be reduced, either if the initial pressure is too high or if it is desired to have a small flow of blood to test suturing, by releasing the ratchet teeth 5a from the lip 16 as previously described and by maintaining gradually reduced, finger pressure on the arms 2 and 3.

The clamp 1 may be completely released by disengaging the ratchet teeth 5a from the lip 16 and permitting the arms 2 and 3 to spring apart or by deliberately spreading the arms 2 and 3 apart manually.

Thus, the clamp of the invention is simple in construction and may be made relatively easily and inexpensively. A blood vessel may be readily inserted in the clamp and is engaged only by relatively soft material of the strip 8. Furthermore, the pressure on a blood vessel may be readily adjusted, and when the clamp is at least partially closed, a blood vessel cannot be displaced sideways out of the clamp.

Although a single embodiment of the present invention has been described and illustrated, it will be apparent to those skilled in the art that various modifications may be made without departing from the principles of the invention.

What is claimed is:

1. A surgical clamp comprising a pair of arms, each arm being interconnected at one end to one end of the other arm by a flexible, resilient member urging said arms apart and each said arm having an end opposite to said one end thereof, said member permitting said arms to be moved toward each other until they are generally parallel, one of said arms having an intermediate, part engaging clamping portion facing the other of said arms and the other of said arms having an intermediate, part engaging, clamping portion facing the clamping portion of said one arm, a layer of resilient material on each of the facing surfaces of said clamping portions, said material being softer than the material of said clamping portions, and releasable ratchet means at the opposite end of one of said arms and extending toward and being engageable with the other of said arms adjacent the opposite end of the last-mentioned other arm, when the arms are moved toward each other, for holding said arms in fixed relative positions.

2. A surgical clamp as set forth in claim 1 wherein said arms, said member and said ratchet means are made of a plastics material and in one piece.

3. A surgical clamp as set forth in claim 1 or 2 wherein said clamping portion of each arm extends upwardly from each arm toward the other arm.

4. A surgical clamp as set forth in claim 3 further comprising a first projection at an end of a clamping portion of one of said arms, said projection being at the end of said last-mentioned clamping portion nearest said member and extending toward the other arm, and a second projection at an end of the clamping portion of said last-mentioned other arm, said second projection being at the end of said last-mentioned clamping portion farthest from said member and extending toward said last-mentioned one arm, said first and second projections obstructing sidewise movement of a part from between the clamping portions when the clamping portions engage a part therebetween.

5. A surgical clamp as set forth in claim 1 wherein said layer of resilient material is a single strip which overlies the facing surfaces of both clamping portions, said clamping portions have tapered slots therein and said strip has projections extending into and interfitting with the walls of said slots.

6. A surgical clamp as set forth in claim 1 wherein said ratchet means is a ratchet extending from said last-mentioned arm toward said last-mentioned other arm, and said last-mentioned other arm has an opening therein for receiving said ratchet, said ratchet having teeth and being formed to urge said teeth toward and engage a sidewall of said opening.

* * * * *